United States Patent
Berrocal Flores et al.

(10) Patent No.: US 11,596,649 B2
(45) Date of Patent: Mar. 7, 2023

(54) COMPOSITION IN POWDER FORM COMPRISING IRON AND PROBIOTIC BACTERIA

(71) Applicant: NESTEC S.A., Vevey (CH)

(72) Inventors: Rafael Berrocal Flores, St-Legier Vaud (CH); Bertrand Bourqui, Bern (CH); Joeska Husny, Bern (CH); Antoine Jean-Pierre Roux, Niederhunigen (CH)

(73) Assignee: Societe des Produits Nestle S.A., Vevey (CH)

( * ) Notice: Subject to any disclaimer, the term of this patent is extended or adjusted under 35 U.S.C. 154(b) by 767 days.

(21) Appl. No.: 16/346,609

(22) PCT Filed: Nov. 9, 2017

(86) PCT No.: PCT/EP2017/078717
§ 371 (c)(1),
(2) Date: May 1, 2019

(87) PCT Pub. No.: WO2018/087208
PCT Pub. Date: May 17, 2018

(65) Prior Publication Data
US 2019/0282614 A1  Sep. 19, 2019

(30) Foreign Application Priority Data

Nov. 10, 2016  (EP) ..................................... 16198292

(51) Int. Cl.
| | | |
|---|---|---|
| *A61K 33/26* | (2006.01) | |
| *A23L 33/16* | (2016.01) | |
| *A23L 33/135* | (2016.01) | |
| *A23L 33/00* | (2016.01) | |
| *A61K 9/00* | (2006.01) | |
| *A61K 9/14* | (2006.01) | |
| *A23D 7/00* | (2006.01) | |
| *A23K 20/20* | (2016.01) | |
| *A61K 35/00* | (2006.01) | |

(52) U.S. Cl.
CPC .............. *A61K 33/26* (2013.01); *A23D 7/003* (2013.01); *A23K 20/20* (2016.05); *A23L 33/00* (2016.08); *A23L 33/135* (2016.08); *A23L 33/16* (2016.08); *A23L 33/40* (2016.08); *A61K 9/0095* (2013.01); *A61K 9/141* (2013.01); *A23V 2002/00* (2013.01); *A23V 2200/3204* (2013.01); *A23V 2250/1592* (2013.01); *A61K 2035/115* (2013.01)

(58) Field of Classification Search
CPC ......... A23D 7/003; A23K 20/20; A23L 33/00; A23L 33/135; A23L 33/16; A23L 33/40; A23V 2002/00; A23V 2200/3204; A23V 2250/1592; A61K 2035/115; A61K 33/26; A61K 9/0095; A61K 9/141
See application file for complete search history.

(56) References Cited

U.S. PATENT DOCUMENTS

2010/0316769 A1* 12/2010 Czarnecki-Maulden .................... A23L 33/15
426/62
2015/0230499 A1*  8/2015 Ollagnier ................ A23P 10/30
426/71

FOREIGN PATENT DOCUMENTS

| CN | 1913905 A | 2/2007 |
|---|---|---|
| CN | 102293340 A | 12/2011 |
| CN | 105324033 A | 2/2016 |
| WO | 2007126990 | 11/2007 |

OTHER PUBLICATIONS

Patent Abstract—Patent No. CN 104 206 737 A, Dec. 17, 2014, 3 pages, XP-002769779.
Patent Abstract—Patent No. CN 104 304 803 A, Jan. 28, 2015, 2 pages, XP-002769778.
Chinese Office Action for Appl No. 201780068348.6 dated Jul. 15, 2022.

* cited by examiner

*Primary Examiner* — Blaine Lankford
(74) *Attorney, Agent, or Firm* — K&L Gates LLP (57) ABSTRACT

The present invention relates to a composition in powder form comprising probiotic bacteria and at least one iron source selected from ferrous citrate, ferric citrate, ferrous sulphate monohydrate and mixtures thereof. Ferrous citrate, ferric citrate, ferrous sulphate monohydrate and mixtures thereof advantageously do not cause significant inhibition or reduction in the viability of the bacteria and thus these iron sources are advantageously used to fortify a composition in powder form comprising probiotic bacteria.

10 Claims, 5 Drawing Sheets

**Impact of iron source on *B. longum* survival**

| Composition | Dissolved ferrous sulphate in spray-dried form | Ferrous sulphate monohydrate |
|---|---|---|
| 5 mg Fe2+ per 100g composition | -0.01 | -0.12 |
| 25 mg Fe2+ per 100g composition | 0.78 | 0.18 |
| 50 mg Fe2+ per 100g composition | 1.94 | 0.34 |

Loss [Log CFU per gram of composition]

COMPOSITION IN POWDER FORM COMPRISING IRON AND PROBIOTIC BACTERIA

CROSS REFERENCE TO RELATED APPLICATIONS

The present application is a National Stage of International Application No. PCT/EP2017/078717, filed on Nov. 9, 2017, which claims priority to European Patent Application No. 16198292.1, filed on Nov. 10, 2016, the entire contents of which are being incorporated herein by reference.

FIELD OF THE INVENTION

The present invention relates to a composition in powder form comprising probiotic bacteria and at least one iron source selected from ferrous citrate, ferric citrate, ferrous sulphate monohydrate and mixtures thereof. Ferrous citrate, ferric citrate, ferrous sulphate monohydrate and mixtures thereof advantageously do not cause significant reduction in the viability of the bacteria and thus these iron sources are advantageously used to fortify a composition in powder form comprising probiotic bacteria.

BACKGROUND OF THE INVENTION

Beneficial bacteria and in particular probiotic bacteria are added to a wide range of products and namely to products in powder form to be reconstituted with a liquid, such as nutritional compositions for infant, young children, pregnant or lactating women, elderly people or people in need of specific nutrition due to an adverse medical condition. Such products usually comprise a large variety of macro- and micro-nutrients, in order to meet the nutritional needs of the consumer. For nutritional purposes, it is of paramount importance that the consumer gets appropriate amounts of the probiotic bacteria and of the other nutrients.

A particularly important micro-nutrient is iron. Worldwide, iron deficiency is one of the most prevalent nutrient deficiencies. In humans, iron is essential for the functioning of a large number of biological processes such as oxygen binding and transport, gene regulation, neurological function, immune function and regulation of cell growth and differentiation. Iron deficiency may result in anaemia, as well as a variety of health problems, such as impairment of thyroid, immune and mental functions, physical performance, cognitive development, increased sensitivity to insulin and fatigue. Iron deficiency is especially widespread in pregnant and lactating women, as well as in children.

Fortification of foods with iron is one approach to combatting iron deficiency. Therefore, the inclusion of an added iron source in dietary compositions or supplements, particularly dietary compositions or supplements for infants, small children, women pre-pregnancy, during pregnancy and/or during lactation, is highly desirable. Diverse iron compounds have been used as iron fortifying agents in food products and in nutritional supplements. For example, ferrous sulphate is widely used, owing to its relatively low price and high bioavailability.

However, the present inventors have found that a number of iron compounds, when used to fortify a composition containing a probiotic bacteria, have a deleterious effect on the viability of the probiotic bacteria (see also co-pending application PCT/EP2016/063170).

In most cases, the benefits of probiotic bacteria are obtained only when the bacteria are alive at the time of consumption. Thus, in order to compensate for the loss of viable probiotic bacteria and to ensure that appropriate amounts of such bacteria are delivered to the consumer, the probiotic bacteria are usually over-dosed in the product. This solution is however not fully satisfying, because overdosing is very costly and generates waste.

Thus, an object of the present invention is to provide compositions comprising a probiotic bacteria and an added iron source, in which the viability of the probiotic bacteria is not compromised by the presence of the added iron source.

SUMMARY OF THE INVENTION

The present inventors have surprisingly found that ferrous citrate, ferric citrate, ferrous sulphate monohydrate and mixtures thereof, when used as an iron source in a composition containing probiotic bacteria, do not cause a reduction in the viability of the bacteria.

In a first aspect, the invention provides a composition in powder form comprising at least one probiotic bacteria and an iron source, characterized in that the iron source is selected from ferrous citrate, ferric citrate, ferrous sulphate monohydrate and mixtures thereof.

In a second aspect, the invention relates to the use of an iron source selected from ferrous citrate, ferric citrate, ferrous sulphate monohydrate and mixtures thereof for the fortification of a composition in powder form, said composition comprising at least one probiotic bacteria.

In a third aspect, the invention provides a process for producing a composition in powder form comprising
  a) providing a first composition in powder form;
  b) admixing to the first composition in powder form an iron source to form a second composition in powder form; and
  c) admixing at least one probiotic bacteria to the first composition in powder form before or at the same time as the iron source or admixing at least one probiotic bacteria to the second composition in powder form, after the addition of the iron source,
characterized in that the iron source is selected from ferrous citrate, ferric citrate, ferrous sulphate monohydrate and mixtures thereof.

In a fourth aspect, the invention provides a method for producing a product comprising reconstituting in a liquid a composition in powder form comprising at least one probiotic bacteria and an iron source, characterized in that the iron source is selected from ferrous citrate, ferric citrate, ferrous sulphate monohydrate and mixtures thereof.

In a fifth aspect, the invention provides a product obtainable or obtained by the method of the invention.

In a sixth aspect, the invention provides a composition of the invention for use in a method of providing a nutrition to an individual.

In a seventh aspect, the invention provides an edible composition in powder form comprising at least one probiotic bacteria and an iron source, for use in the prevention, reduction and/or treatment of iron deficiency in an individual, characterized in that the iron source is selected from ferrous citrate, ferric citrate, ferrous sulphate monohydrate and mixtures thereof.

In an eighth aspect, the invention provides a method for reducing and/or preventing the loss of probiotic bacteria during reconstitution of a composition in powder form comprising at least one probiotic bacteria and an added iron source, characterized in that ferrous citrate, ferric citrate, ferrous sulphate monohydrate or a mixture thereof is used as the added iron source.

DETAILED DESCRIPTION OF THE INVENTION

Definitions

As used herein, the term "probiotic bacteria" refers to live bacterial cell preparations with a beneficial effect on the health or well-being of the host [Salminen S, et al., "Probiotics: how they should be defined", Trends Food Sci. Technol, (1999), 10, 107-10].

Bacteria are considered as "live" when they are able to multiply under controlled culture conditions and form colonies or suspensions or when the microorganism metabolic activity and/or membrane integrity can be established using methods known to the person skilled in the art, such as for example flow cytometry. Dried probiotic bacteria are considered as live when they are able to multiply and/or when membrane integrity can be established, as described above, after reconstitution of the bacteria with a liquid, such as an aqueous liquid, preferably water.

For the purpose of the present invention, "reconstitution" refers to dissolution or suspension of a powder in a liquid such as an aqueous liquid, preferably water, a specific reconstitution medium as used in analytical microbiology, or a drink like milk or juice. The liquid used for reconstitution may be cold or warm. Preferably it refers to reconstitution with an aqueous liquid, preferably with water.

An "aqueous liquid" is intended for the purpose of the present invention as a liquid comprising at least one aqueous phase. It can be for example an emulsion, an aqueous solution or dispersion or water. Preferably it is an oil-in-water emulsion, an aqueous solution or suspension or water. More preferably it is an aqueous solution or suspension or water. Most preferably it is water.

The term "iron" is herein intended as designating either $Fe^{2+}$ or $Fe^{3+}$, depending on the iron source used.

An "added iron source" is intended for the purpose of the present invention as a ferrous or ferric compound added to the composition for the sole benefit of iron supplementation. Depending on its nature, the composition may comprise iron coming from other ingredients, for example from milk, fruit, vegetable, cereal or fibre components. Iron present in such ingredients is not intended here as an "added iron source", because it is inherently present in an ingredient that is not primarily added for its iron content, but for its overall nutritional value.

An iron source is intended for the purpose of the present invention as being "substantially the only added iron source" in the composition, provided that other added iron sources are used in a sufficiently small amount not to cause a statistically significant loss of viable probiotic bacteria. The skilled person can assess whether a statistically significant loss of viable bacteria is caused by applying the method described in the examples of the present application and applying commonly known statistical techniques for the analysis of the results.

The term "nutritional composition" designates a product intended to provide a complete nutrition or a supplemental nutrition to an individual (i.e. to fulfil essential nutritional needs of such individual) and in which the prominent objective is to provide nutrition. A nutritional composition aims at providing specific nutrients to an individual having special nutritional needs, such as infants, young children, pregnant or lactating women, elderly people or people with adverse medical condition requiring special food (e.g. tube feeding compositions or compositions for paediatric subjects). Products in which the hedonic aspect is prominent and nutritional qualities are not of primary importance are excluded from the "nutritional products". Nutritional compositions preferably comprise proteins, fats, carbohydrates and diverse micro-nutrients.

In the present invention, the term "infant" means a child between birth and 12 months of age. The terms "young child" refer to a child between 12 months and 5 years of age, preferably between 12 months and 3 years of age.

The expression "infant formula" as used herein refers to a foodstuff intended for particular nutritional use by infants and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The infant formulas can encompass the starter infant formulas and the follow-up or follow-on formulas. Generally a starter formula is for infants from birth as breast-milk substitute. A follow-up or follow-on formula is given from the 6th month onwards. It constitutes the principal liquid element in the progressively diversified diet of this category of person. It is to be understood that infants can be fed solely with infant formulas, or that the infant formula can be used as a supplement or complement of human milk.

The "growing-up milks" (or GUMs) are given from one year onwards. It is generally a milk-based beverage adapted for the specific nutritional needs of young children.

The expression "baby food" means a foodstuff intended for particular nutritional use by infants or children such as young children, during the first years of life.

The expression "infant cereal composition" means a cereal-based foodstuff intended for particular nutritional use by infants or children such as young children, during the first years of life.

The term "fortifier" refers to nutritional compositions suitable for mixing with breast milk or infant formula. The "breast milk" should be understood as the mother's milk or the colostrum of the mother or a donor's milk or the colostrum of a donor's milk.

The term "supplement" refers to a composition that can be used to supplement, or complement, the nutrition of an individual.

The term "prebiotic" means non-digestible carbohydrates that beneficially affect the host by selectively stimulating the growth and/or the activity of healthy bacteria in the colon of humans (Gibson G R, Roberfroid M B. Dietary modulation of the human colonic microbiota: introducing the concept of prebiotics. J Nutr. 1995; 125:1401-12).

Composition

The composition of the present invention is a composition in powder form comprising at least one probiotic bacteria and an iron source, said iron source being selected from ferrous citrate, ferric citrate, ferrous sulphate monohydrate and mixtures thereof.

The present inventors have surprisingly found that, within the many constituents of a complete nutritional composition, such as an infant formula, added iron was responsible for significant loss of probiotic bacteria in the reconstituted composition. Also, the present inventors have identified that three specific iron salts could advantageously be used as nutritional sources of iron, in combination with probiotic bacteria, without causing significant loss of viability of such probiotic bacteria. These sources of iron are ferrous citrate, ferric citrate and ferrous sulphate monohydrate.

In a preferred embodiment, the iron source is selected from ferrous sulphate monohydrate, ferrous citrate and mixtures thereof. These iron sources are particularly advantageous due to their good bioavailability. Most preferably the iron source is ferrous sulphate monohydrate, which has the best bioavailability.

Ferrous sulphate exists in various forms of hydration (mono-, tetra-, penta-, hexa- and heptahydrate). The tetra-, penta- and hexahydrate forms being unstable, they are rarely used commercially. Ferrous sulphate monohydrate (also sometimes designated as "dried") and ferrous sulphate heptahydrate are both stable and crystalline forms of ferrous sulphate that are commonly used commercially.

Ferrous sulphate is also commonly used in powdered products in the form of a spray-dried powder formed by spray-drying dissolved ferrous sulphate in a carrier, such as maltodextrin (hereinafter referred to as "dissolved ferrous sulphate in spray-dried form"). In this case, the ferrous sulphate is typically dissolved at acidic pH, such as pH2, before being admixed with a carrier and dried. In dissolved ferrous sulphate in spray-dried form, the iron and sulphate ions remain dissociated from each other and are dispersed in the amorphous carrier.

Now, the present inventors have found that ferrous sulphate heptahydrate and dissolved ferrous sulphate in spray-dried form both cause significant loss of viability of probiotic bacteria, whereas no significant loss of viability of probiotic bacteria is observed with the monohydrate form of ferrous sulphate. Without wishing to be bound by theory, the present inventors believe that its crystalline state and its low level of hydration both significantly delay the dissolution of ferrous sulphate monohydrate in aqueous media. Also, the present inventors have identified that probiotic bacteria were particularly sensitive to iron at the time of reconstituting the powdered composition with a liquid. At the time of reconstitution of the powdered composition with a liquid, the long dissolution time of ferrous sulphate monohydrate is believed to let sufficient time for the probiotic bacteria to re-hydrate before it is faced with free iron, thus reducing the viability loss of the probiotic bacteria.

This positive effect is observed when ferrous sulphate monohydrate is used as such and when ferrous sulphate monohydrate is dispersed in an amorphous matrix, provided that the crystalline structure and the level of hydration of ferrous sulphate monohydrate remain. Such ingredient with ferrous sulphate monohydrate dispersed in a matrix can be obtained by mixing the crystalline iron salt in a carrier solution and spray-drying the carrier. The process shall be carried out without dissolving the crystalline iron salt by keeping a sufficiently high pH, preferably by keeping a non-acidic pH. The person skilled in the art can routinely assess if a product or ingredient comprises ferrous sulphate monohydrate with its crystalline structure and its level of hydration. Indeed, several analytical techniques can be employed for identification of ferrous sulphate monohydrate, including polarised microscopy and NIR spectroscopy.

The use of ferrous sulphate monohydrate is particularly advantageous, in that it is characterized at the same time by good bioavailability and by low detrimental impact on probiotic bacteria viability. Ferrous sulphate monohydrate is commercially available, for example from Dr. Paul Lohmann GmbH KG, Emmerthal, Germany or DSM Nutritional Products, Heerlen, the Netherlands.

Also owing to the low level of free iron liberated at the time of reconstitution, ferrous citrate and ferric citrate do not significantly impair the viability of probiotic bacteria. Thus, these two iron salts can advantageously be used as iron sources in a composition in powder form comprising probiotic bacteria. Both ferrous citrate and ferric citrate are commercially available, for example from Dr. Paul Lohmann GmbH KG, Emmerthal, Germany or DSM Nutritional Products, Heerlen, the Netherlands.

In a preferred embodiment, at least 50 wt %, more preferably at least 60 wt %, more preferably at least 70 wt %, more preferably at least 80 wt %, even more preferably at least 90 wt % of the added iron is in the form of an iron source as defined above. Even more preferably, the iron source as defined above is substantially the only added iron source in the composition. Most preferably, the iron source as defined above is the only added iron source in the composition.

The added iron source is preferably present in an amount such as to provide from 1 to 300 mg, preferably 1 to 250 mg, more preferably 1 to 200 mg, more preferably 1 to 100 mg, even more preferably 1 to 75 mg, most preferably 1 to 50 mg of iron per 100 g of composition, based on the total dry weight of the composition.

Any live probiotic bacteria can be used in the composition of the invention. The examples provided in the present application show that the selected iron sources do not impair the viability of diverse bacterial genera. The effect is not strain-specific and can be applied to a wide range of bacterial strains.

Examples of probiotic bacteria that can be present in the composition of the present invention include bifidobacteria, lactobacilli, lactococci, enterococci, streptococci, *Leuconostoc*, *Escherichia*, propionibacteria, or combinations thereof, preferably it is a bacteria of the *Lactobacillus* or of the *Bifidobacterium* genus.

Preferably the probiotic bacteria is selected among the species *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus rhamnosus, Lactobacillus johnsonii, Lactobacillus plantarum, Lactobacillus fermentum, Lactobacillus reuteri, Lactococcus lactis, Streptococcus thermophilus, Lactococcus diacetylactis, Lactococcus cremoris, Lactobacillus delbrueckii* subsp. *bulgaricus, Lactobacillus delbrueckii* subsp. *lactis, Lactobacillus helveticus, Escherichia coli, Enterococcus faecium, Leuconostoc pseudomesenteroides, Bifidobacterium bifidum, Lactobacillus gasseri, Lactobacillus sakei, Streptococcus salivarius*, as well as any of their subspecies and/or mixtures thereof.

More preferably, it is selected from the species *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus rhamnosus, Lactobacillus johnsonii, Lactobacillus plantarum, Lactobacillus fermentum, Lactobacillus reuteri, Lactobacillus delbrueckii* subsp. *bulgaricus, Lactobacillus delbrueckii* subsp. *lactis, Lactobacillus helveticus, Bifidobacterium bifidum, Lactobacillus gasseri, Lactobacillus sakei* and mixtures thereof.

Examples of bacterial strains that can advantageously be present in the composition include *Bifidobacterium longum* (deposited as ATCC BAA-999), *Bifidobacterium longum* (deposited as CNCM I-2618), *Bifidobacterium breve* (deposited as CNCM I-3865), *Bifidobacterium lactis* (deposited as CNCM I-3446), *Lactobacillus johnsonii* (deposited as CNCM I-1225), *Lactobacillus paracasei* (deposited as CNCM I-2116), *Lactobacillus rhamnosus* (deposited as CGMCC 1.3724), *Streptococcus thermophilus* (deposited as CNCM I-1422), *Streptococcus thermophilus* (deposited as CNCM I-4153), *Streptococcus thermophilus* (deposited as CNCM I-1985), *Streptococcus thermophilus* (deposited as CNCM I-3915), *Lactobacillus casei* (deposited as CNCM I-1518), *Lactobacillus casei* (deposited as ACA-DC 6002), *Escherichia coli* Nissle (deposited as DSM 6601), *Lactobacillus bulgaricus* (deposited as CNCM I-1198), *Lactococcus lactis* (deposited as CNCM I-4154), or combinations thereof.

More preferred bacterial strains include *Bifidobacterium longum* (deposited as ATCC BAA-999), *Bifidobacterium longum* (deposited as CNCM I-2618), *Bifidobacterium breve* (deposited as CNCM I-3865), *Bifidobacterium lactis* (deposited as CNCM I-3446), *Lactobacillus johnsonii* (deposited as CNCM I-1225), *Lactobacillus paracasei* (deposited as CNCM I-2116), *Lactobacillus rhamnosus* (deposited as CGMCC 1.3724), *Lactobacillus casei* (deposited as CNCM I-1518), *Lactobacillus casei* (deposited as ACA-DC 6002), *Streptococcus thermophilus* (deposited as CNCM I-3915) and *Lactobacillus bulgaricus* deposited as (CNCM I-1198) or combinations thereof.

In a further preferred embodiment the probiotic bacteria is selected from *Bifidobacterium longum* (deposited as ATCC BAA-999), *Lactobacillus rhamnosus* (deposited as CGMCC 1.3724) and *Lactobacillus paracasei* (deposited as CNCM I-2116) and mixtures thereof.

The probiotic bacteria is preferably present in the composition in an amount of at least 5E+06 CFU per gram of composition, on a dry weight basis, preferably 5E+06 to 1E+12 CFU per gram of composition, more preferably 5E+06 to 5E+11 CFU per gram of composition, most preferably 5E+06 to 5E+10 CFU per gram of composition.

The selected probiotic bacteria may be cultured according to any suitable method and prepared for addition to the composition by known techniques such as freeze-drying or spray-drying for example. Alternatively, bacterial preparations can be bought from specialist suppliers such as DSM, Dupont Danisco, Morinaga, Institut Rosell, Christian Hansen and Valio, already prepared in a suitable form for addition to a composition in powder form.

The composition in powder from may be in the form of free powder or in the form of compressed powder, such as in the form of a tablet. Preferably the composition in powder form is not intended to be used in the form of a powder, but is to be reconstituted in a liquid, preferably in an aqueous liquid, most preferably in water, before use.

Preferred compositions in powder form of the invention include a food or beverage product, an animal feed product, a nutritional supplement for human or animal, a pharmaceutical composition or a cosmetic composition.

In another preferred embodiment, the composition in powder form is an edible composition.

Food and beverage products include all products intended to be consumed orally by human beings, for the purpose of providing nutrition and/or pleasure. In a preferred embodiment, the product is a nutritional composition. More preferably it is a nutritional composition selected from an infant formula, a growing-up milk, a baby food, an infant cereal composition, a fortifier, a supplement and a nutritional composition for pregnant or lactating women. More preferably, it is selected from an infant formula, a growing-up milk, an infant cereal composition and a nutritional composition for pregnant or lactating women. Even more preferably, it is selected from an infant formula, a growing-up milk and an infant cereal composition. Most preferably, it is an infant formula or a growing-up milk.

The product can also be in the form of an animal food product or a nutritional supplement for animals. Preferably, the animal is a mammal. Examples of animals include primates, cows, sheep, goats, horses, dogs, cats, rabbits, rats, mice, fish, birds and the like.

Nutritional supplements in powder form include free powder or compressed powder supplements, and typically encompass supplements to be dissolved in water or to be sprinkled on wet food or in a beverage. Such supplements are intended to provide additional nutrients and/or a health benefit to the subject consuming it, as well as other beneficial ingredients, including probiotic bacteria and iron. A supplement according to the present invention can be used for providing nutrients and/or a health benefit to human beings, as well as to animals, as defined above. Nutritional supplements include for example powder supplements to be added to breast milk, for example for premature or low birth weight infants. It also includes supplements for women pre-pregnancy, during pregnancy and/or during lactation.

Pharmaceutical compositions are compositions intended to treat or to prevent an adverse medical condition in a subject in need thereof.

Cosmetic compositions are typically intended for an aesthetic effect on the body and may preferably be administered by oral route.

The composition, preferably the nutritional composition, preferably comprises protein, carbohydrates, fats, vitamins and/or other minerals. Preferably, it comprises all of these types of nutrients.

The proteins may be intact or hydrolysed (extensively or partially hydrolysed). The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well as small amounts of oils containing high quantities of preformed arachidonic acid and docosahexaenoic acid such as fish oils or microbial oils.

The composition according to the present invention may contain a carbohydrate source, such as lactose, maltodextrin, starch and mixtures thereof. The composition according to the present invention may also contain a particular type of carbohydrates: prebiotics. The prebiotics that may be used in accordance with the present invention are not particularly limited and include all food substances that promote the growth of probiotics or health beneficial micro-organisms in the intestines. Preferably, they may be selected from the group consisting of oligosaccharides, optionally containing fructose, galactose, and mannose; dietary fibers, in particular soluble fibers, soy fibers; inulin; or mixtures thereof. Some examples of prebiotics are fructo-oligosaccharides (FOS), galacto-oligosaccharides (GOS), isomalto-oligosaccharides (IMO), xylo-oligosaccharides (XOS), arabino-xylo oligosaccharides (AXOS), mannan-oligosaccharides (MOS), inulin, polydextrose, glycosylsucrose (GS), lactosucrose (LS), lactulose (LA), palatinose-oligosaccharides (PAO), malto-oligosaccharides, gums and/or hydrolysates thereof, pectins and/or hydrolysates thereof. In a particular embodiment, the prebiotics may be fructooligosaccharides and/or inulin. Suitable commercial products that can be used include combinations of FOS with inulin such as the product sold by BENEO under the trademark Orafti, or polydextrose sold by Tate & Lyle under the trademark STA-LITE®.

The prebiotics can also be a BMO (bovine's milk oligosaccharide) and/or a HMO (human milk oligosaccharide) such as N-acetylated oligosaccharides, sialylated oligosaccharides, fucosylated oligosaccharides and any mixtures thereof.

A particular example of prebiotic is a mixture of galacto-oligosaccharide(s), N-acetylated oligosaccharide(s) and sialylated oligosaccharide(s) in which the N-acetylated oligosaccharide(s) represent 0.5 to 4.0 wt % of the oligosaccharide mixture, the galacto-oligosaccharide(s) represent 92.0 to 98.5 wt % of the oligosaccharide mixture and the sialylated oligosaccharide(s) represent 1.0 to 4.0 wt % of the oligosaccharide mixture. For example a composition for use according to the invention can contain from 2.5 to 15.0 wt % CMOS-GOS on a dry matter basis with the proviso that the composition comprises at least 0.02 wt % of an N-acetylated oligosaccharide, at least 2.0 wt % of a galacto-oligosaccharide and at least 0.04 wt % of a sialylated oligosaccharide. WO2006087391 and WO2012160080 provide some examples of production of such an oligosaccharide mixture.

The composition of the invention may also contain all vitamins, minerals and other micronutrients, understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended target group.

Process for Producing a Composition in Powder Form

In an embodiment, the present invention relates to a process for producing a composition in powder form comprising
  a) providing a first composition in powder form;
  b) admixing an iron source with the first composition in powder form to obtain a second composition in powder form; and
  c) admixing at least one probiotic bacteria to the first composition in powder form before or at the same time as the iron source or admixing at least one probiotic bacteria to the second composition in powder form, after the addition of the iron source,
characterized in that the iron source is selected from ferrous citrate, ferric citrate, ferrous sulphate monohydrate and mixtures thereof.

The composition in powder form, the iron source and the probiotic bacteria are as defined in any of the embodiments described above in the "composition" section.

The first composition in powder form can be prepared using any method known in the art, such as for example spray-drying. In such a method, the ingredients of the composition are mixed in a wet mix and sprayed in a drying tower to form a powder. Sensitive ingredients, like minerals or vitamins for example, may also be added in dry form before, at the same time or after addition of the iron source and/or of the probiotic bacteria. For example, it is common that the iron source is added to the first composition in powder form as a trace element premix comprising diverse minerals and vitamins.

The probiotic bacteria is preferably added in the form of a pre-blend comprising a carrier and optionally protective agents. Carriers for probiotic bacteria are well-known to the person skilled in the art of incorporating probiotic bacteria into products. The carrier is preferably a carbohydrate, such as for example maltodextrin. A wide variety of protective agents are known to the person skilled in the art. Particularly suitable protective agents are those described in the co-pending patent application PCT/EP16/065359 of the same applicant.

The steps of admixing the probiotic bacteria and the step of admixing the iron source may be performed using any method known in the art for mixing such types of ingredients with a powder composition. For example the admixture can be performed by dry-mixing, by direct addition in the spray-drying tower, in a fluid bed, coater or agglomerator or at final stage of extrusion or roller drying. Preferably, the probiotic bacteria and/or the iron source are admixed with the composition in powder form by dry-mixing or by addition in a fluid bed. Most preferably, the probiotic bacteria and/or the iron source are admixed with the composition in powder form by dry-mixing.

In a preferred embodiment, at least 50 wt %, more preferably at least 60 wt %, more preferably at least 70 wt %, more preferably at least 80 wt %, even more preferably at least 90 wt % of the added iron in the composition is in the form of an iron source as defined above. Even more preferably, the iron source as defined above is substantially the only added iron source in the composition. Most preferably, the iron source as defined above is the only added iron source in the composition.

Use of Specific Iron Sources for the Fortification of a Composition in Powder Form Ferrous citrate, ferric citrate, ferrous sulphate monohydrate and mixtures thereof can advantageously be used for the fortification of a composition in powder form comprising at least one probiotic bacteria. Such iron sources advantageously provide bioavailable iron, while causing no significant loss of viability of probiotic bacteria during reconstitution of the powder with a liquid, such as water.

Ferrous sulphate monohydrate being one of the most bioavailable iron sources (average bioavailability of 100% in human described in Hurrell, Iron Fortification of Foods, Acad. Press Inc., 1985), ferrous sulphate monohydrate is the preferred iron source for the purpose of the invention.

Ferrous citrate is also advantageously characterized by good bioavailability (average bioavailability of 74% in human described in Hurrell, Iron Fortification of Foods, Acad. Press Inc., 1985). For this reason, it is preferred to ferric citrate, which has a good bioavailability in rat (75%), but is less bioavailable in human (31%), as indicated in Hurrell, Iron Fortification of Foods, Acad. Press Inc., 1985).

In another embodiment, the present invention relates to a method for fortifying a composition in powder form comprising at least one probiotic bacteria, said method comprising the steps of a) providing a first composition in powder form;
b) admixing to the first composition in powder form an iron source to produce a second composition in powder form; and
c) admixing at least one probiotic bacteria to the first composition in powder form before or at the same time as the iron source or admixing at least one probiotic bacteria to the second composition in powder form, after the addition of the iron source, wherein the iron source is selected from ferrous citrate, ferric citrate, ferrous sulphate monohydrate and mixtures thereof.

The first composition in powder form, the second composition in powder form and the process steps are as defined in the section above related to the process for producing the composition of the invention. Also, the composition in powder form, the iron source and the probiotic bacteria are as described above in any embodiment of the "composition" section.

In a preferred embodiment, at least 50 wt %, more preferably at least 60 wt %, more preferably at least 70 wt %, more preferably at least 80 wt %, even more preferably at least 90 wt % of the added iron in the composition is in the form of an iron source as defined above. Even more preferably, the iron source as defined above is substantially the only added iron source in the composition. Most preferably, the iron source as defined above is the only added iron source in the composition.

A Composition for Use in a Method to Prevent, Reduce and/or Treat Iron Deficiency The composition of the invention being fortified with a bioavailable iron source, as described above, the present invention also relates to a composition for use in a method to prevent, reduce and/or treat iron deficiency in an individual. For this purpose, ferrous citrate and ferrous sulphate monohydrate are preferred, ferrous sulphate monohydrate being the most preferred iron source.

Method for Producing a Product

The invention relates to a method for producing a product, preferably an edible product, comprising reconstituting in a liquid a composition in powder form comprising at least one probiotic bacteria and an iron source, characterized in that the iron source is selected from ferrous citrate, ferric citrate, ferrous sulphate monohydrate and mixtures thereof.

The composition in powder form, the probiotic bacteria and the iron source are as defined in any of the embodiments described above.

The use of an iron source selected from ferrous citrate, ferric citrate, ferrous sulphate monohydrate and mixtures thereof is particularly advantageous when the composition in powder form is reconstituted in a liquid. The present inventors have found that probiotic bacteria were particularly sensitive at the time of rehydration and that loss of viability was particularly acute when the composition in powder form was reconstituted with a liquid such as water. The present inventors have also discovered that ferrous citrate, ferric citrate, ferrous sulphate monohydrate and mixtures thereof did not cause significant loss of viability of probiotic bacteria at that critical moment, contrary to common sources of iron, such as ferrous sulphate heptahydrate or dissolved ferrous sulphate in spray-dried form.

Reconstitution is preferably carried out with an aqueous liquid, most preferably water. The amount of liquid, preferably water, added for the reconstitution depends on the type of product that is prepared. What is key for the purpose of the present invention is that enough liquid is added to reconstitute the probiotic bacteria to its natural moisture content.

Product

The invention also relates to a product, preferably an edible product, obtainable or obtained by the method described above. The product comprises the composition in powder form, as defined in any embodiment of the present invention, reconstituted in a liquid. Preferably, it is reconstituted in an aqueous liquid, preferably in water.

Preferably, the product is a nutritional product, obtained by reconstitution of a nutritional composition as described above.

Method for Providing a Nutrition

A method for providing a nutrition to an individual comprising feeding the individual with an edible product of the invention, preferably with a nutritional product of the invention, is also contemplated. The product used in this method is a food or beverage composition. Preferably, it is a nutritional composition as defined above. Such products are particularly advantageous because they comprise a bioavailable source of iron and stable concentrations of probiotic bacteria, as no significant loss of probiotic bacteria is caused by the added iron source.

In an embodiment the method comprises the steps of
a) reconstituting an edible composition in powder form according to any of the embodiments of the invention; and
b) feeding an individual with the reconstituted composition.

In an embodiment, the individual is an individual having an iron deprivation or an individual at risk of developing an iron deprivation. In another embodiment, the individual is an infant, a young child or a pregnant or lactating mother.

In another preferred embodiment the edible composition is a nutritional composition.

In an another embodiment, the present invention relates to a composition according to the present invention for use in a method of providing a nutrition to an individual. Preferably, such individual is as defined above.

Method for Preventing or Reducing the Loss of Probiotic Bacteria

The invention relates to a method for reducing or preventing the loss of probiotic bacteria during reconstitution of a composition in powder form comprising at least one probiotic bacteria and an added iron source, characterized in that ferrous citrate, ferric citrate, ferrous sulphate monohydrate or a mixture thereof is used as the added iron source.

The probiotic bacteria, the added iron source and the composition in powder form are as described in any embodiment of the "composition" section.

In a preferred embodiment, ferrous citrate, ferric citrate, ferrous sulphate monohydrate or a mixture thereof represents at least 50 wt %, more preferably at least 60 wt %, more preferably at least 70 wt %, more preferably at least 80 wt %, even more preferably at least 90 wt % of the added iron in the composition. More preferably ferrous citrate, ferric citrate, ferrous sulphate monohydrate or a mixture thereof is substantially the only added iron source used in the composition. Most preferably ferrous citrate, ferric citrate, ferrous sulphate monohydrate or a mixture thereof is the only added iron source in the composition. In other words, the composition comprises no other ferrous or ferric compound added as an iron source in the composition.

The present inventors have shown that by using ferrous citrate, ferric citrate or ferrous sulphate monohydrate instead of other commonly added iron sources, such as ferrous sulphate heptahydrate or dissolved ferrous sulphate in spray-dried form, the loss of probiotic bacteria at the time of reconstitution of the composition could be prevented or at least significantly reduced.

The added iron source has an important impact on the survival of the probiotic bacteria, whereas the impact of iron sources present as part of an ingredient that is not intended mainly for the purpose of iron supplementation is much smaller, owing to the complexity of such ingredients. Among other reasons, the iron they contain is usually not found as free iron at the time of reconstituting the composition and thus has reduced potential harmful effects on probiotic bacteria.

The present invention will now be described in further details by the way of the following examples.

EXAMPLE 1

Effect of Iron Source on Survival of *Lactobacillus rhamnosus*

Five powder compositions (Samples A to D) were prepared, each comprising dried *Lactobacillus rhamnosus* (deposited as CGMCC 1.3724), an iron source and 100 g of maltodextrin. The composition of the five samples is summarized in Table 1 below.

The Samples were produced as follows. The maltodextrin, the dried probiotic powder and the iron source were added together in a 500 mL plastic beaker and mixed for 5 minutes at 34 rpm using a Turbula® T2F dry mixer (WAB, Switzerland). An amount of 25 g of freshly mixed sample was diluted 1/10 in an aqueous tryptone salt solution supplemented with anti-foaming agent at 37° C. After 5 minutes of homogenization using a Masticator® (IUL, Spain), decimal dilutions were performed. The appropriate dilution resulting in 30-300 colonies after incubation was then transferred to a petri dish and mixed with MRS agar according to the pour plate method. Once solidified the plates were incubated at 37° C. under aerobic conditions. After 48 h of incubation the colonies present on the plates were counted.

TABLE 1

Composition of Samples A to D

| Ingredient | Sample A | Sample B | Sample C | Sample D | Sample E |
| --- | --- | --- | --- | --- | --- |
| Dried *L. rhamnosus*[1] | 90 mg | 90 mg | 90 mg | 90 mg | 90 mg |
| Iron source: dissolved ferrous sulphate in spray-dried form[2] | 0 mg | 119 mg | 0 mg | 357 mg | 0 mg |
| Iron source: ferrous sulphate monohydrate[3] | 0 mg | 0 mg | 31 mg | 0 mg | 92 mg |
| Maltodextrin | 100 g | 100 g | 100 g | 100 g | 100 g |
| Amount of $Fe^{2+}$ provided by the iron source | 0 mg | 10 mg | 10 mg | 30 mg | 30 mg |

Figure 1:
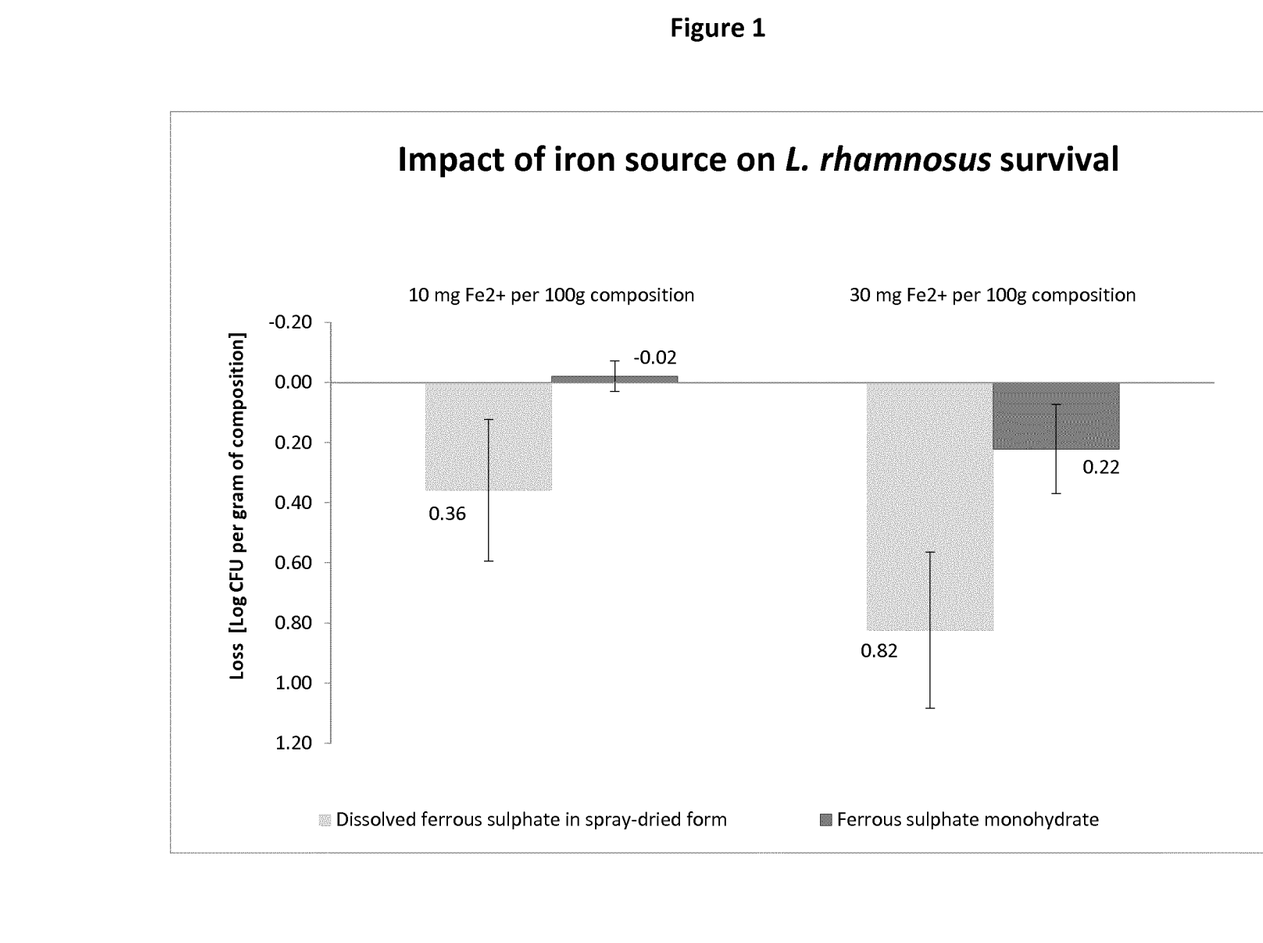
FIG. 1: Graphic representation of the loss of viability of Lactobacillus rhamnosus (deposited as CGMCC 1.3724) in compositions having respectively 10 and 30 mg of $Fe^{2+}$ per 100 g of a model composition based on maltodextrin. Two different iron sources are compared: dissolved ferrous sulphate in spray-dried form and ferrous sulphate monohydrate. The loss of viable Lactobacillus rhamnosus is significantly lower with ferrous sulphate monohydrate, at both iron concentrations.

[1] Spray-dried *Lactobacillus rhamnosus* (deposited as CGMCC 1.3724) in maltodextrin matrix. The total amount of live bacteria in the composition is of 3.1E+10 CFU/g.
[2] Obtained by dissolving ferrous sulphate in water at pH 2 and spray-drying in a maltodextrin matrix. This iron source contains 8.4 wt % of $Fe^{2+}$.
[3] Ferrous sulphate monohydrate, dried fine powder FCC8 containing 32.7 wt % of $Fe^{2+}$, origin: Dr. Paul Lohmann The results are summarized in FIG. 1. It is clear from this graph that significant loss of live *L. rhamnosus* was observed in the reconstituted compositions when ferrous sulphate heptahydrate was used. In contrast, when ferrous sulphate monohydrate was used in the same conditions, with the same amount of *L. rhamnosus* and same amount of $Fe^{2+}$, no significant loss of *L. rhamnosus* was observed.

EXAMPLE 2

Effect of Iron Source on Survival of *Bifidobacterium longum*

Seven powder compositions (Samples E to K) were prepared, each comprising dried *Bifidobacterium longum* (deposited as ATCC BAA-999), an iron source and 100 g of maltodextrin. The composition of the seven samples is summarized in Table 2 below.

TABLE 2

Composition of Samples E to K

| Ingredient | Sample E | Sample F | Sample G | Sample H | Sample I | Sample J | Sample K |
|---|---|---|---|---|---|---|---|
| Dried *B. longum*[1] | 130 mg | 130 mg | 130 mg | 130 mg | 130 mg | 130 mg | 130 mg |
| Iron source: dissolved ferrous sulphate in spray-dried form[2] | 0 mg | 60 mg | 0 mg | 298 mg | 0 mg | 595 mg | 0 mg |
| Iron source: ferrous sulphate monohydrate[3] | 0 mg | 0 mg | 15 mg | 0 mg | 76 mg | 0 mg | 153 mg |
| Maltodextrin | 100 g | 100 g | 100 g | 100 g | 100 g | 100 g | 100 g |
| Amount of $Fe^{2+}$ provided by the iron source | 0 mg | 5 mg | 5 mg | 25 mg | 25 mg | 50 mg | 50 mg |

[1] Spray-dried *Bifidobacterium longum* (deposited as ATCC BAA-999) in maltodextrin matrix. The total amount of live bacteria in the composition is of 3.1E+10 CFU/g.
[2] Obtained by dissolving ferrous sulphate in water at pH 2 and spray-drying in a maltodextrin matrix. This iron source contains 8.4 wt % of $Fe^{2+}$.
[3] Ferrous sulphate monohydrate, dried fine powder FCC8 containing 32.7 wt % of $Fe^{2+}$, origin: Dr. Paul Lohmann The Samples were produced as follows. The maltodextrin, the dried probiotic powder and the iron source were added together in a 500 mL plastic beaker and mixed for 5 minutes at 34 rpm using a Turbula® T2F dry mixer (WAB, Switzerland). An amount of 25 g of freshly mixed sample was diluted ¹⁄₁₀ in an aqueous tryptone salt solution supplemented with anti-foaming agent at 37° C. After 5 minutes of homogenization using a Masticator® (IUL, Spain), decimal dilutions were performed. The appropriate dilution resulting in 30-300 colonies after incubation was then transferred to a petri dish and mixed with RCA agar according to the pour plate method. Once solidified the plates were incubated at 37° C. under anaerobic conditions. After 48 h of incubation the colonies present on the plates were counted.

Figure 2:
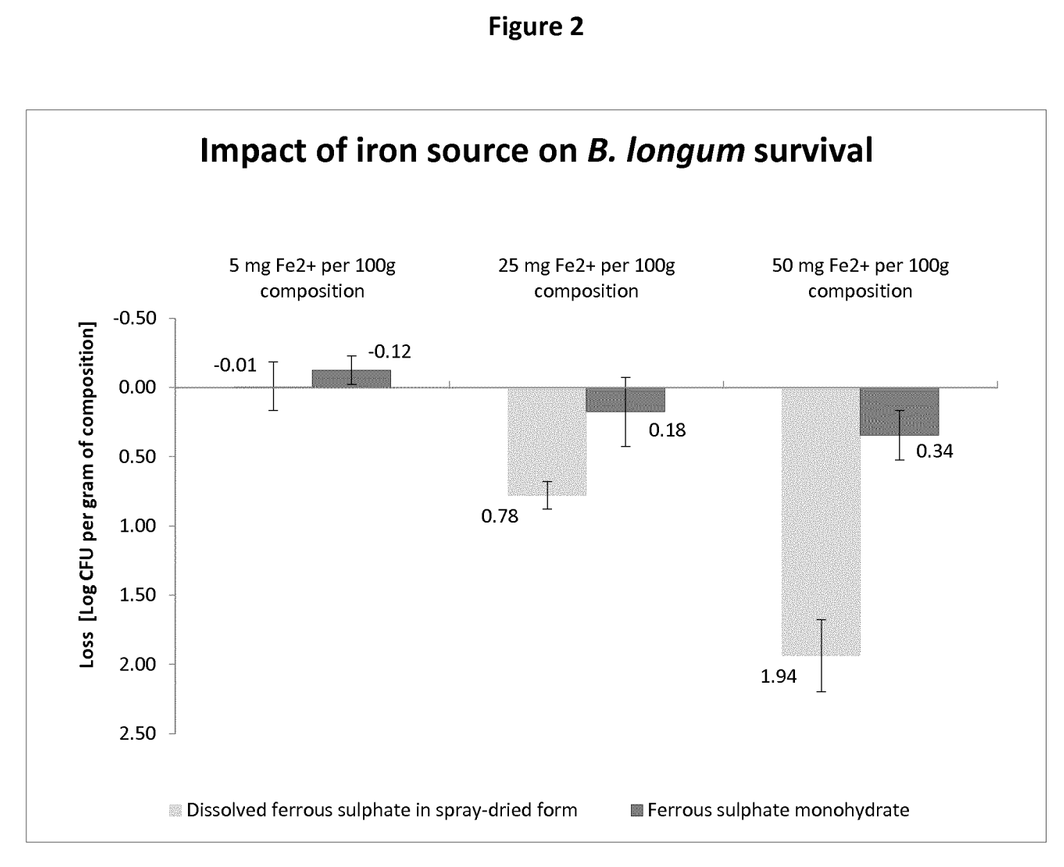
FIG. 2: Graphic representation of the loss of viability of Bifidobacterium longum (deposited as ATCC BAA-999) in compositions having respectively 5, 25 and 50 mg of $Fe^{2+}$ per 100 g of a model composition based on maltodextrin. Two different iron sources are compared: dissolved ferrous sulphate in spray-dried form and ferrous sulphate monohydrate. The loss of viable Bifidobacterium longum is significantly lower with ferrous sulphate monohydrate, at all iron concentrations.

The results are summarized in FIG. 2. It is clear from this graph that significant loss of live *Bifidobacterium longum* is observed in the reconstituted compositions when ferrous sulphate heptahydrate was used. In contrast, when ferrous sulphate monohydrate was used in the same conditions, with the same amount of *Bifidobacterium longum* and same amount of $Fe^{2+}$, no significant loss of *Bifidobacterium longum* was observed.

EXAMPLE 3

Effect of Iron Source on Survival of *Lactobacillus paracasei*

Seven powder compositions (Samples L to R) were prepared, each comprising dried *Lactobacillus paracasei* (deposited as CNCM I-2116), an iron source and 100 g of maltodextrin. The composition of the seven samples is summarized in Table 3 below.

The Samples were produced as follows. The maltodextrin, the dried probiotic powder and the iron source were added together in a 500 mL plastic beaker and mixed for 5 minutes at 34 rpm using a Turbula® T2F dry mixer (WAB, Switzerland). An amount of 25 g of freshly mixed sample was diluted ¹⁄₁₀ in an aqueous tryptone salt solution supplemented with anti-foaming agent at 37° C. After 5 minutes of homogenization using a Masticator® (IUL, Spain), decimal dilutions were performed. The appropriate dilution resulting in 30-300 colonies after incubation was then transferred to a petri dish and mixed with MRS agar according to the pour plate method. Once solidified the plates were incubated at 37° C. under aerobic conditions. After 48 h of incubation the colonies present on the plates were counted.

Figure 3:
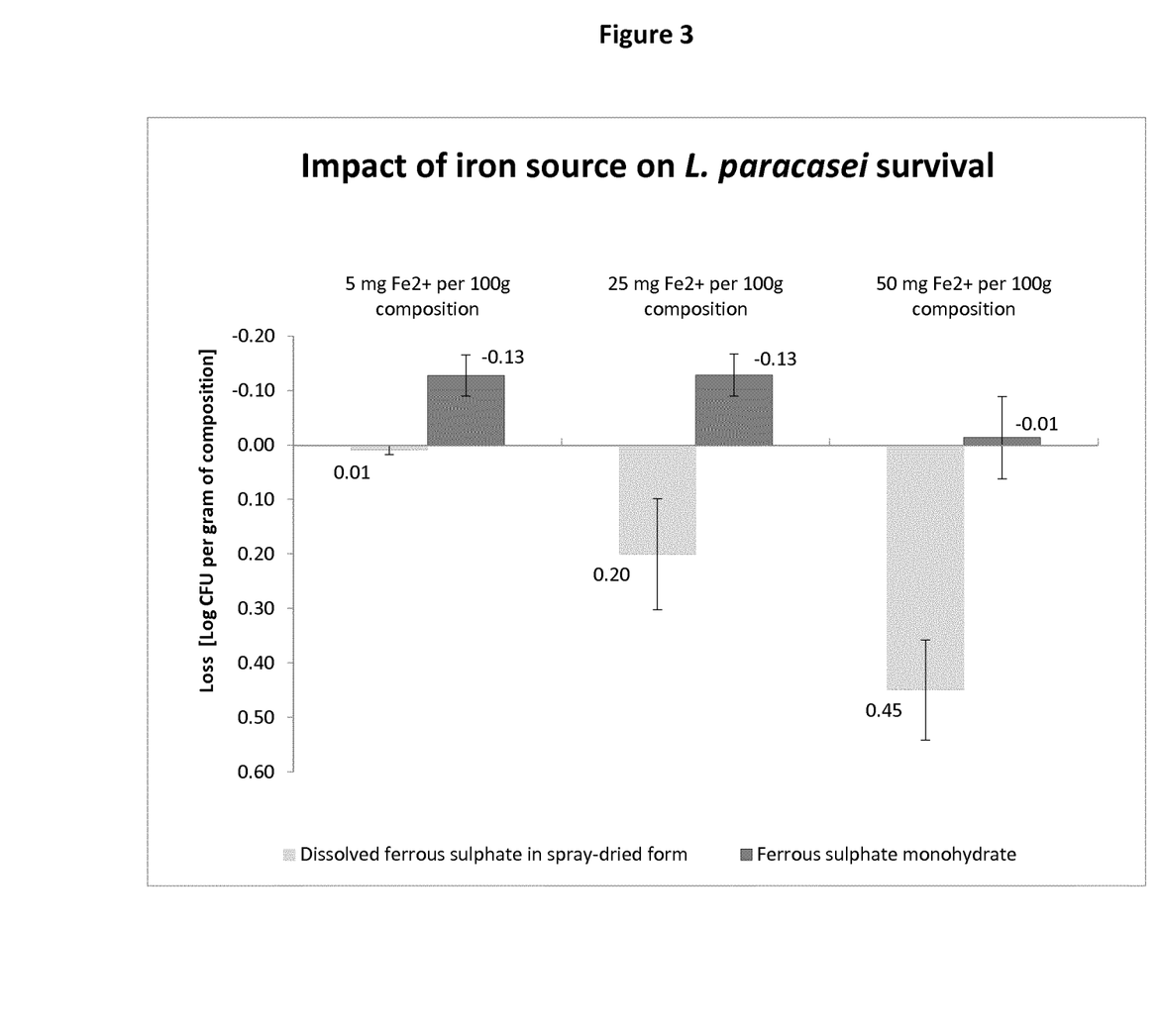
FIG. 3: Graphic representation of the loss of viability of Lactobacillus paracasei (deposited as CNCM 1-2116) in compositions having respectively 5, 25 and 50 mg of $Fe^{2+}$ per 100 g of a model composition based on maltodextrin. Two different iron sources are compared: dissolved ferrous sulphate in spray-dried form and ferrous sulphate monohydrate. The loss of viable Lactobacillus paracasei is significantly lower with ferrous sulphate monohydrate, at all iron concentrations.

The results are summarized in FIG. 3. It is clear from this graph that significant loss of live *Lactobacillus paracasei* was observed in the reconstituted compositions when dissolved ferrous sulphate in spray-dried form was used. In contrast, when ferrous sulphate monohydrate was used in the same conditions, with the same amount of *Lactobacillus paracasei* and same amount of $Fe^{2+}$, no significant loss of *Lactobacillus paracasei* was observed.

TABLE 3

Composition of Samples L to R

| Ingredient | Sample L | Sample M | Sample N | Sample O | Sample P | Sample Q | Sample R |
|---|---|---|---|---|---|---|---|
| Dried *L. paracasei*[1] | 85 mg | 85 mg | 85 mg | 85 mg | 85 mg | 85 mg | 85 mg |
| Iron source: dissolved ferrous sulphate in spray-dried form[2] | 0 mg | 60 mg | 0 mg | 298 mg | 0 mg | 595 mg | 0 mg |
| Iron source: ferrous sulphate monohydrate[3] | 0 mg | 0 mg | 15 mg | 0 mg | 76 mg | 50 mg | 153 mg |
| Maltodextrin | 100 g | 100 g | 100 g | 100 g | 100 g | 100 g | 100 g |
| Amount of $Fe^{2+}$ provided by the iron source | 0 mg | 5 mg | 5 mg | 25 mg | 25 mg | 50 mg | 50 mg |

[1] Spray-dried *Lactobacillus paracasei* (deposited as CNCM I-2116) in maltodextrin matrix. The total amount of live bacteria in the composition is of 3.1E+10 CFU/g.
[2] Obtained by dissolving ferrous sulphate in water at pH 2 and spray-drying in a maltodextrin matrix. This iron source contains 8.4 wt % of $Fe^{2+}$.
[3] Ferrous sulphate monohydrate, dried fine powder FCC8 containing 32.7 wt % of $Fe^{2+}$, origin: Dr. Paul Lohmann

EXAMPLE 4

Effect of Iron Source on Survival of *Lactobacillus rhamnosus*

Five powder compositions (Samples S to W) were prepared, each comprising dried *Lactobacillus rhamnosus* (deposited as CGMCC 1.3724), an iron source and 100 g of an infant formula powder. The composition of the five samples is summarized in Table 4 below.

TABLE 4

Composition of Samples S to W

| Ingredient | Sample S | Sample T | Sample U | Sample V | Sample W |
|---|---|---|---|---|---|
| Dried *L. rhamnosus*[1] | 90 mg | 90 mg | 90 mg | 90 mg | 90 mg |
| Iron source: ferrous sulphate heptahydrate[2] | 0 mg | 119 mg | 0 mg | 357 mg | 0 mg |
| Iron source: crystalline ferrous sulphate monohydrate[3] | 0 mg | 0 mg | 31 mg | 0 mg | 92 mg |
| Infant formula powder[4] | 100 g | 100 g | 100 g | 100 g | 100 g |
| Amount of $Fe^{2+}$ provided by the iron source | 0 mg | 10 mg | 10 mg | 30 mg | 30 mg |

[1] Spray-dried *Lactobacillus rhamnosus* (deposited as CGMCC 1.3724) in maltodextrin matrix. The total amount of live bacteria in the composition is of 3.1E+10 CFU/g.
[2] Obtained by dissolving ferrous sulphate in water at pH 2 and spray-drying in a maltodextrin matrix. This iron source contains 8.4 wt % of $Fe^{2+}$.
[3] Ferrous sulphate monohydrate, dried fine powder FCC8 containing 32.7 wt % of $Fe^{2+}$, origin: Dr. Paul Lohmann
[4] Nestogen 1, origin: Nestlé

The Samples were produced as follows. The infant formula powder, the dried probiotic powder and the iron source were added together in a 500 mL plastic beaker and mixed for 5 minutes at 34 rpm using a Turbula® T2F dry mixer (WAB, Switzerland). An amount of 25 g of freshly mixed sample was diluted 1/10 in an aqueous tryptone salt solution supplemented with anti-foaming agent at 37° C. After 5 minutes of homogenization using a Masticator® (IUL, Spain), decimal dilutions were performed. The appropriate dilution resulting in 30-300 colonies after incubation was then transferred to a petri dish and mixed with MRS agar according to the pour plate method. Once solidified the plates were incubated at 37° C. under aerobic conditions. After 48 h of incubation the colonies present on the plates were counted.

Figure 4:
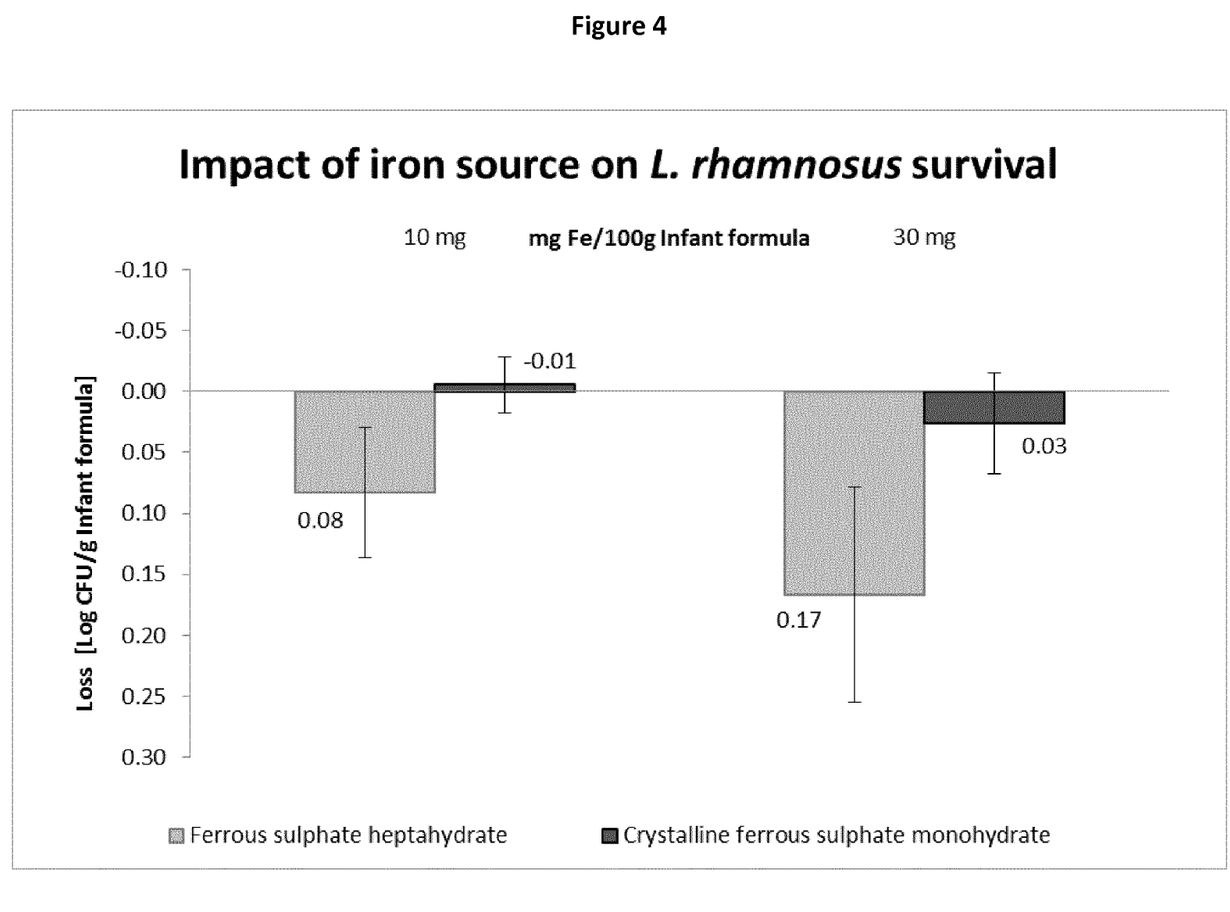
FIG. 4: Graphic representation of the loss of viability of Lactobacillus rhamnosus (deposited as CGMCC 1.3724) in compositions having respectively 10 and 30 mg of $Fe^{2+}$ per 100 g of an infant formula composition. Two different iron sources are compared: dissolved ferrous sulphate in spray-dried form and ferrous sulphate monohydrate. The loss of viable Lactobacillus rhamnosus is significantly lower with ferrous sulphate monohydrate, at both iron concentrations.

The results are summarized in FIG. 4. It is clear from this graph that significant loss of live *L. rhamnosus* was observed in the reconstituted compositions when ferrous sulphate heptahydrate was used. In contrast, when ferrous sulphate monohydrate was used in the same conditions, with the same amount of *L. rhamnosus* and same amount of $Fe^{2+}$, no significant loss of *L. rhamnosus* was observed. These results obtained in a complete infant formula composition are consistent with those obtained in example 1 in a model composition comprising maltodextrin. This shows that ferrous sulphate monohydrate is advantageous over ferrous sulphate heptahydrate, even in a complex product matrix.

EXAMPLE 5

Effect of Iron Source on Survival of *Bifidobacterium longum*

Five powder compositions (Samples X to Z and AA to BB) were prepared, each comprising dried *Bifidobacterium longum* (deposited as ATCC BAA-999), an iron source and 100 g of an infant formula powder. The composition of the five samples is summarized in Table 5 below.

TABLE 5

Composition of Samples X to Z and AA to BB

| Ingredient | Sample X | Sample Y | Sample Z | Sample AA | Sample BB |
|---|---|---|---|---|---|
| Dried *B. longum* | 100 mg | 100 mg | 100 mg | 100 mg | 100 mg |
| Iron source: ferrous sulphate heptahydrate[1] | 0 mg | 298 mg | 0 mg | 595 mg | 0 mg |
| Iron source: crystalline ferrous sulphate monohydrate[2] | 0 mg | 0 mg | 77 mg | 0 mg | 154 mg |
| Infant formula powder[4] | 100 g | 100 g | 100 g | 100 g | 100 g |

TABLE 5-continued

Composition of Samples X to Z and AA to BB

| Ingredient | Sample X | Sample Y | Sample Z | Sample AA | Sample BB |
|---|---|---|---|---|---|
| Amount of $Fe^{2+}$ provided by the iron source | 0 mg | 25 mg | 25 mg | 50 mg | 50 mg |

[1] Spray-dried *Bifidobacterium longum* (deposited as ATCC BAA-999) in maltodextrin matrix. The total amount of live bacteria in the composition is of 3.1E+10 CFU/g.
[2] Obtained by dissolving ferrous sulphate in water at pH 2 and spray-drying in a maltodextrin matrix. This iron source contains 8.4 wt % of $Fe^{2+}$.
[3] Ferrous sulphate monohydrate, dried fine powder FCC8 containing 32.7 wt % of $Fe^{2+}$, origin: Dr. Paul Lohmann
[4] Nestogen 1, origin: Nestlé

The Samples were produced as follows. The infant formula powder, the dried probiotic powder and the iron source were added together in a 500 mL plastic beaker and mixed for 5 minutes at 34 rpm using a Turbula® T2F dry mixer (WAB, Switzerland). An amount of 25 g of freshly mixed sample was diluted 1/10 in an aqueous tryptone salt solution supplemented with anti-foaming agent at 37° C. After 5 minutes of homogenization using a Masticator® (IUL, Spain), decimal dilutions were performed. The appropriate dilution resulting in 30-300 colonies after incubation was then transferred to a petri dish and mixed with RCA agar according to the pour plate method. Once solidified the plates were incubated at 37° C. under anaerobic conditions. After 48 h of incubation the colonies present on the plates were counted.

Figure 5:
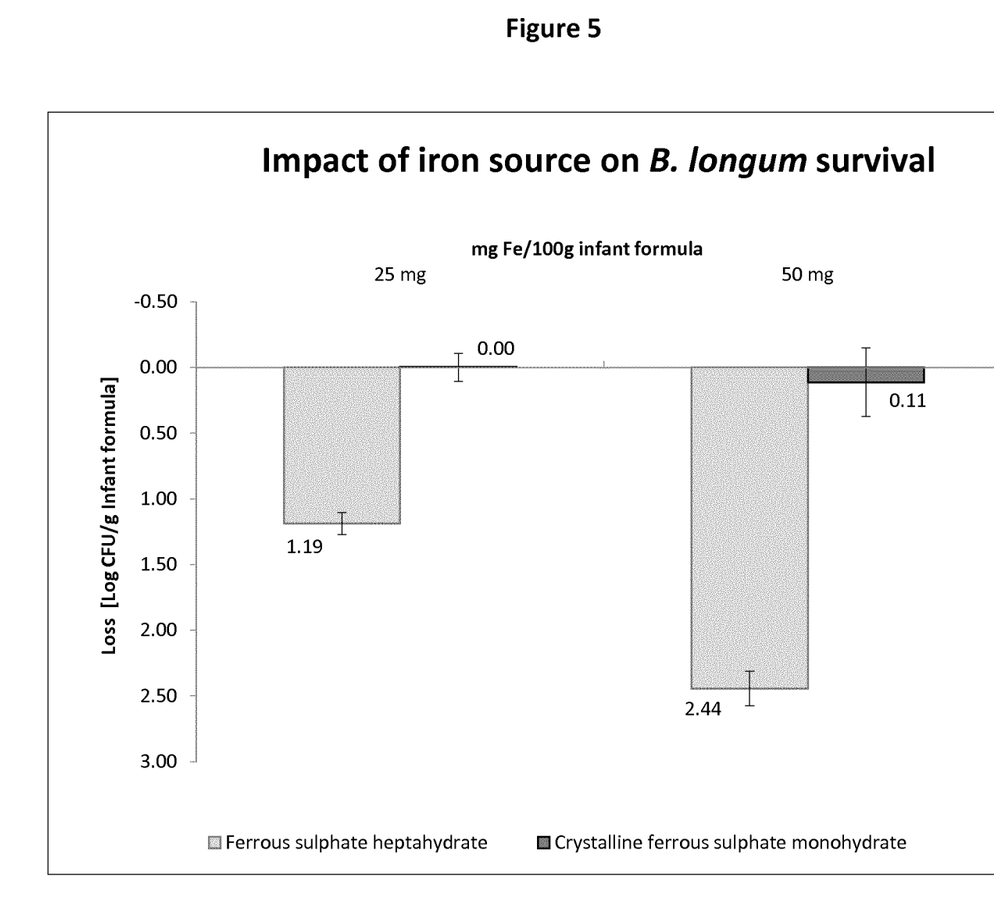
FIG. 5: Graphic representation of the loss of viability of Bifidobacterium longum (deposited as ATCC BAA-999) in compositions having respectively 25 and 50 mg of $Fe^{2+}$ per 100 g of an infant formula composition. Two different iron sources are compared: dissolved ferrous sulphate in spray-dried form and ferrous sulphate monohydrate. The loss of viable Bifidobacterium longum is significantly lower with ferrous sulphate monohydrate, at all iron concentrations.

The results are summarized in FIG. 5. It is clear from this graph that significant loss of live *Bifidobacterium longum* is observed in the reconstituted compositions when ferrous sulphate heptahydrate was used. In contrast, when ferrous sulphate monohydrate was used in the same conditions, with the same amount of *Bifidobacterium longum* and same amount of $Fe^{2+}$, no significant loss of *Bifidobacterium longum* was observed. These results obtained in a complete infant formula composition are consistent with those obtained in example 2 in a model composition comprising maltodextrin. This shows that ferrous sulphate monohydrate is advantageous over ferrous sulphate heptahydrate, even in a complex product matrix.

The invention claimed is:

1. A composition in powder form, the composition comprising at least one probiotic bacteria and ferrous sulphate monohydrate.

2. The composition according to claim 1, wherein the composition is an edible composition.

3. The composition according to claim 1, wherein the composition is to be reconstituted with a liquid before use.

4. The composition according to claim 1, wherein the composition in powder form is a nutritional composition.

5. The composition according to claim 4, wherein the nutritional composition is selected from the group consisting of an infant formula, a growing-up milk, an infant cereal composition, a fortifier, a supplement and a nutritional composition for pregnant or lactating women.

6. The composition according to claim 1, wherein the ferrous sulphate monohydrate is present in an amount to provide 1 to 300 mg of iron per 100 g of the composition.

7. The composition according to claim 1, wherein the ferrous sulphate monohydrate is present in an amount to provide 1 to 50 mg of iron per 100 g of the composition.

8. The composition according to claim 1, wherein the composition comprises at least 5E+06 CFU of the at least one probiotic bacteria per gram of the composition.

9. The composition according to claim 1, wherein the composition in powder from is in a form of free powder or in a form of compressed powder.

10. The composition according to claim 1, wherein the composition further comprises at least one of protein, carbohydrates, fats, vitamins and additional minerals.

* * * * *